United States Patent [19]
Lorenz et al.

[11] Patent Number: 5,646,290
[45] Date of Patent: Jul. 8, 1997

[54] THIAZOLYLISOINDOLENINE DYESTUFFS

[75] Inventors: Manfred Lorenz, Köln; Klaus Wilfried Wanken, Leverkusen, both of Germany

[73] Assignee: Bayer Aktiengesellschaft, Leverkusen, Germany

[21] Appl. No.: 444,133

[22] Filed: May 18, 1995

[30] Foreign Application Priority Data

May 25, 1994 [DE] Germany ............... 44 18 148.5
Jan. 31, 1995 [DE] Germany ............... 195 02 943.7

[51] Int. Cl.$^6$ ........................... C07D 514/00
[52] U.S. Cl. ............................. 548/159
[58] Field of Search ....................... 518/159

[56] References Cited

U.S. PATENT DOCUMENTS

| | | | |
|---|---|---|---|
| Re. 31,986 | 9/1985 | Lotsch | 548/159 X |
| 3,499,908 | 3/1970 | Vollman et al. | 548/159 X |
| 3,646,033 | 2/1972 | Leister et al. | 548/159 X |
| 4,051,099 | 9/1977 | von der Crone | 548/159 X |
| 4,166,179 | 8/1979 | Lotsch | 548/159 X |
| 4,426,533 | 1/1984 | Rochat et al. | 548/159 X |
| 4,481,272 | 11/1984 | Eckell et al. | 548/159 X |
| 4,599,113 | 7/1986 | Lotsch et al. | 548/159 X |
| 4,645,539 | 2/1987 | Lotsch et al. | |
| 5,177,209 | 1/1993 | Wagner et al. | 548/159 X |
| 5,326,872 | 7/1994 | Wagner et al. | 548/159 X |
| 5,393,568 | 2/1995 | Valente et al. | 548/159 X |

FOREIGN PATENT DOCUMENTS

| | | |
|---|---|---|
| 0061094 | 9/1982 | European Pat. Off. . |
| 0062614 | 10/1982 | European Pat. Off. . |
| 0132818 | 2/1985 | European Pat. Off. . |
| 0358148 | 3/1990 | European Pat. Off. . |
| 0510436 | 10/1992 | European Pat. Off. . |
| 1537299 | 8/1968 | France . |
| 2307008 | 11/1976 | France . |
| 955178 | 6/1956 | Germany . |

OTHER PUBLICATIONS

Derwent Abstract of JP 2–113,074 (Apr. 1990).

*Primary Examiner*—Robert Gerstl
*Attorney, Agent, or Firm*—Sprung Horn Kramer & Woods

[57] ABSTRACT

Novel thiozolylisoindolenine dyestuffs of the formula (I)

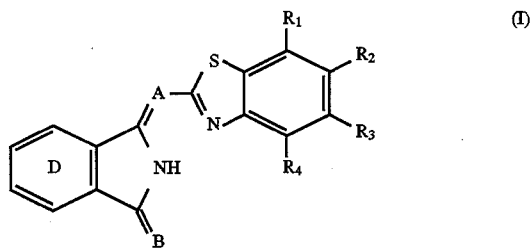

have been found in which

A represents N or a cyanomethylene radical,

B represents a radical of the formula $C(CN)COOR_5$ or $N-R_6$ and the remaining substituents have the meanings given in the description. The invention also relates to mixtures thereof, a process for their preparation and their use for dyeing hydrophobic synthetic materials.

5 Claims, No Drawings

THIAZOLYLISOINDOLENINE DYESTUFFS

The present invention relates to novel thiazolylisoindolenine dyestuffs, mixtures thereof, processes for their preparation and their use for dyeing hydrophobic synthetic materials.

Isoindolenine derivatives have already been described in EP-A 61,094 and been used in electrophotography. DE-A-2,615,394 discloses isoindoline derivatives for colouring thermoplastics in the mould and EP-A-358,148 uses solid isoindolinone and isoindoline compounds for colouring plastics. The dyestuffs from the isoindoline series disclosed in DE-A-1,670,748 are used for dyeing synthetic fibre materials, but they still exhibit unsatisfactory properties in practical application.

Novel dyestuffs of the formula (I)

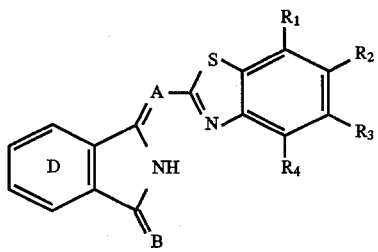

have now been found, in which

A represents N or a cyanomethylene radical,

B represents a radical of the formula $C(CN)COOR_5$ or $N—R_6$, $R_1$ to $R_4$, independently of one another, denote hydrogen, halogen, substituted or unsubstituted $C_1–C_8$-alkyl or $C_5–C_6$-cycloalkyl, uninterrupted or oxygen-interrupted $C_1–C_{10}$-alkoxy, substituted or unsubstituted $C_6–C_{10}$-aryloxy, $CF_3$, or substituted or unsubstituted dialkylamine, or any two adjacent $R_1$ to $R_4$ radicals together with the aromatic ring C atoms form a fused benzene or naphthalene ring which, if desired, may be further substituted, the substituents including, for example, halogen or $C_1–C_4$-alkyl, $R_5$ represents a substituted or unsubstituted, saturated or unsaturated $C_1–C_{20}$-alkyl radical, $C_6–C_{10}$-aryl-$C_1–C_{10}$-alkyl or hetarylalkyl radical, the alkyl radical being uninterrupted or interrupted by oxygen atoms, $R_6$ denotes substituted or unsubstituted $C_5–C_6$-cycloalkyl, $C_5–C_6$-cycloalkyl-$C_1–C_8$-alkyl, $C_6–C_{10}$-aryl-$C_1–C_{10}$-alkyl or $C_1–C_{20}$-alkyl, the latter being uninterrupted or interrupted by oxygen atoms and the ring D being unsubstituted or carrying at least one substituent which together with a further substituent in the O position and the ring C atoms may form a fused benzene or naphthalene ring, with the exception of the dyestuff of the formula

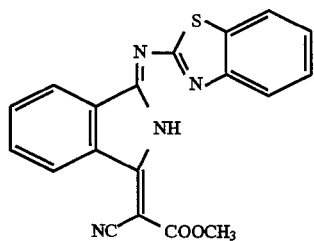

disclosed in EP-A 61,094.

Examples of suitable radicals $R_1$ to $R_4$ are hydrogen, chlorine, bromine, methyl, ethyl, iso-propyl, tert-butyl, methoxy, ethoxy, n-propoxy, n-butoxy, methoxy-ethyl, methoxy-ethoxy-ethyl, ethoxy-ethyl, ethoxy-ethoxy-ethyl, butoxy-ethyl, phenoxy, 2-methyl-phenoxy, 3-methyl-phenoxy, phenoxy-ethoxy, 4-methyl-phenoxy, dimethylamino, diethylamino, bis-(2-cyano-ethyl)-amino.

Examples of suitable radicals $R_5$ are methyl, ethyl, n-propyl, iso-propyl, allyl, n-butyl, n-pentyl, n-hexyl, n-heptyl, n-octyl, n-decyl, 2-methoxy-ethyl, 2-ethoxy-ethyl, 2-isopropoxy-ethyl, 2-butoxy-ethyl, 2-allyloxy-ethyl, 2-(2-methoxy-ethoxy)-ethyl, 2-(2-ethoxy-ethoxy)-ethyl, 2-(2-methoxy-ethoxy)-ethyl, 2-cyano-ethyl, 2-(cyano-ethoxy)-ethyl, 4-(2-cyano-ethoxy)-butyl, 2-ethyl-hexyl, benzyl, phenylethyl, 3-phenylpropyl, phenoxy-ethyl, furfuryl. Suitable branched radicals $R_5$ are preferably those having a methyl side chain, such as, for example, iso-butyl, tert-butyl, iso-pentyl, 1-methoxy-2-propanol, 1-ethoxy-2-propanol.

Examples of suitable radicals $R_6$ are methyl, ethyl, n-propyl, iso-propyl, allyl, n-butyl, n-pentyl, n-hexyl, n-heptyl, n-octyl, n-decyl, 2-ethyl-hexyl, 2-methoxy-ethyl, 2-ethoxy-ethyl, 3-methoxy-propyl, 3-ethoxy-propyl, 3-butoxy-propyl, 3-phenoxy-propyl, 3-(2-phenoxy-ethoxy)-propyl, cyclohexyl, cyclohexylmethyl, benzyl, 2-phenyl-ethyl.

Preference is given to dyestuffs of the formula (I) in which $R_1$ and $R_2$, independently of one another, denote hydrogen, Cl, Br, methyl, ethyl, n-propyl, isopropyl, n-butyl, iso-butyl, tert-butyl, cyclohexyl, $C_1–C_{10}$-alkoxy which is uninterrupted or interrupted by 1 to 2 oxygens, substituted or unsubstituted phenoxy, $CF_3$ or a di($C_1–C_4$)-alkylamino group, $R_3$ and $R_4$ have the meaning of $R_1$ and $R_2$ or together with the ring C atoms form a fused benzene ring, $R_5$ denotes $C_1–C_{12}$-alkyl, $C_6–C_{10}$-aryl-$C_1–C_{10}$-alkyl or hetarylalkyl which is unsubstituted or substituted by Cl, CN or substituted or unsubstituted phenoxy and is uninterrupted or interrupted by 1 to 2 oxygen atoms, $R_6$ denotes saturated or unsaturated $C_1–C_{12}$-alkyl which is unsubstituted or substituted by substituted or unsubstituted phenoxy, and which is uninterrupted or interrupted by 1 to 2 oxygens, and Ring D is unsubstituted or substituted by CN, halogen atoms, in particular 1 to 4 Cl atoms, 1 to 2 $C_1–C_{10}$-alkyl radicals and/or 1 to 2 $C_1–C_{10}$-alkoxy radicals or a phenyl radical, each of which is uninterrupted or interrupted by 1 to 2 oxygen atoms. However, ring D is in particular unsubstituted.

Particularly preferred dyestuffs of the formula (I) are those of the formula (II)

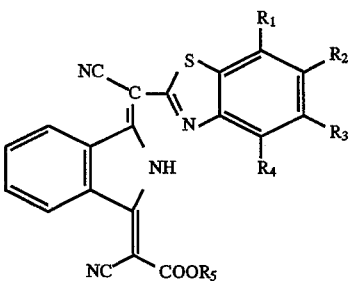

in which $R_1$ to $R_5$ have the above meaning, and, preferably,
$R_1$ to $R_4$, independently of one another, represent hydrogen, chlorine, methyl, ethyl, iso-propyl, tert-butyl, cyclohexyl, methoxy, ethoxy, n-propoxy, n-butoxy, methoxy-ethyl, ethoxy-ethyl, butoxy-ethyl or phenoxy and $R_5$ represents n-butyl, iso-butyl, n- and iso-pentyl, hexyl, octyl, 2-ethyl-hexyl, methoxy-ethyl, ethoxy-ethyl, butoxy-ethyl, butoxy-ethoxy-ethyl.

Preference is also given to dyestuffs of the formula (I) having the formula (III)

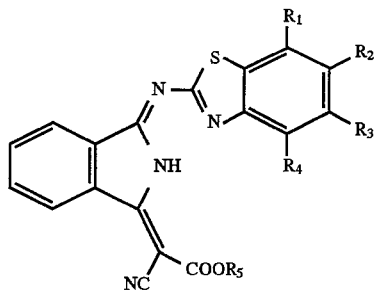

(III)

in which $R_1$ to $R_5$ have the abovementioned meaning and, preferably, $R_1$ to $R_4$, independently of one another, represent hydrogen, chlorine, methyl, ethyl, iso-propyl, tert-butyl, cyclohexyl, methoxy, ethoxy, n-propoxy, n-butoxy, methoxy-ethyl, ethoxy-ethyl, butoxy-ethyl or phenoxy and $R_5$ represents methyl, ethyl, propyl, iso-propyl, allyl, n-butyl, iso-butyl, n- and iso-pentyl, hexyl, octyl, 2-ethyl-hexyl, methoxy-ethyl, ethoxy-ethyl, butoxy-ethyl, butoxy-ethoxy-ethyl.

Preference is also given to dyestuffs of the formula (I) having the formula (IV)

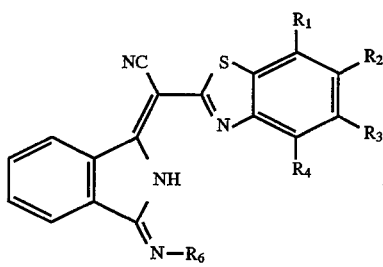

(IV)

in which $R_1$ to $R_4$ and $R_6$ have the abovementioned meaning, and, preferably, $R_1$ to $R_4$, independently of one another, represent hydrogen, chlorine, methyl, iso-propyl, tert-butyl, cyclohexyl, methoxy, ethoxy, n-propoxy, n-butoxy, methoxy-ethyl, ethoxy-ethyl, butoxy-ethyl or phenoxy and $R_6$ represents methyl, ethyl, propyl, iso-propyl, allyl, n-butyl, iso-butyl, n- and iso-pentyl, hexyl, octyl, 2-ethyl-hexyl, cyclohexyl, methoxy-propyl, ethoxy-propyl, 2-phenoxy-ethyl, 3-phenoxypropyl, 2-phenoxy-ethoxy-propyl, phenylethyl.

Moreover, preference is given to dyestuffs of the formula (I) having the following formula

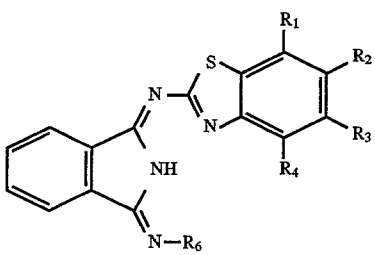

in which $R_1$ to $R_4$ and $R_6$ have the abovementioned meaning and, preferably, $R_1$ to $R_4$, independently of one another, represent hydrogen, chlorine, methyl, iso-propyl, tert-butyl, cyclohexyl, methoxy, ethoxy, n-propoxy, n-butoxy, methoxy-ethyl, ethoxy-ethyl, butoxy-ethyl or phenoxy and $R_6$ represents methyl, ethyl, propyl, iso-propyl, allyl, n-butyl, iso-butyl, n- and iso-pentyl, hexyl, octyl, 2-ethyl-hexyl, cyclohexyl, methoxy-propyl, ethoxy-propyl, 2-phenoxy-ethyl, 3-phenoxypropyl, 2-phenoxy-ethoxy-propyl, phenylethyl.

The invention furthermore provides a process for preparing compounds of the formula (I). In principle, the sum of all dyestuffs falling under formula (I) can be prepared by a uniform process (see, for example, DE-A-1,670,748, DE-A-2,628,409, EP-A-62,614, EP-A-510,436). However, for some compounds of the formula (I), this standard procedure is only moderately successful. This is why subformulae (II), (III) and (IV)

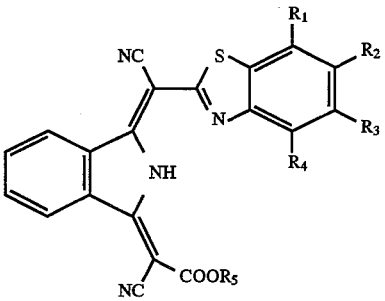

(II)

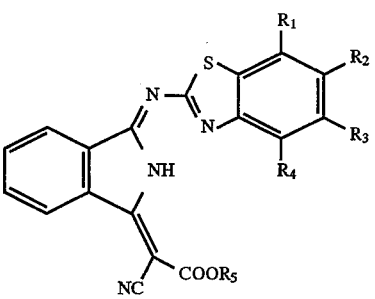

(III)

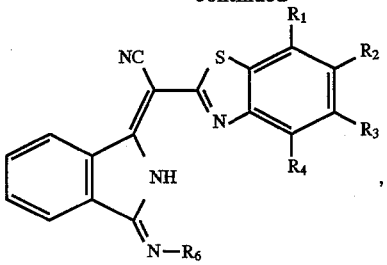

(IV)

in which the radicals $R_1$ to $R_6$ have the abovementioned meaning, have been formulated, for which formulae the best results are obtained with a somewhat different procedure.

The process for preparing compounds of the formula (II) is characterized in that an aminoisoindolenine of the formula (VII)

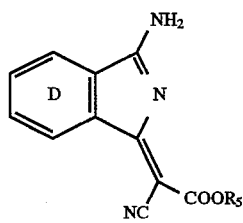

(VII)

is condensed with a 2-cyanomethyl-benzothiazol of the formula (VIII)

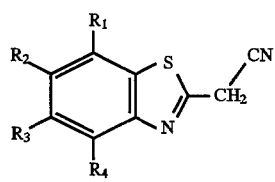

(VIII)

or an aminoisoindolenine of the formula (IX)

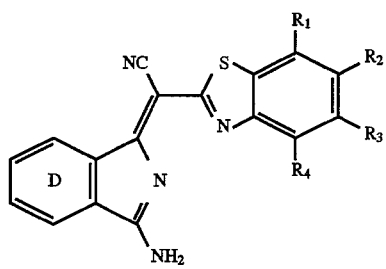

(IX)

is condensed with a cyanoacetic ester of the formula (VI)

$$NC-CH_2-COOR_5$$ (VI)

in which $R_1$ to $R_6$ and D have the abovementioned meaning, the excepted compound also being excepted.

In a preferred embodiment, the process according to the invention for preparing compounds of the formula (II) is carried out in a polar, in particular hydrophilic, organic solvent.

Examples of polar solvents include amides such as dimethylformamide, formamide, dimethylacetamide, N-methylpyrrolidone, furthermore dimethyl sulphoxide, acetonitrile, acetic acid or alcohol, the alcohol used being preferably that which is also used in the acetic esters of the formula (VI) as alcoholic component. Moreover, mixtures of these solvents can also be used.

In this procedure, it is also particularly preferred to add an organic acid. This results in an acceleration of the reaction, an improved crystallinity and a higher yield. Examples of suitable organic acids are lower aliphatic, saturated or unsaturated, mono- or dicarboxylic acids, such as, for example, formic acid, acetic acid, propionic acid, butyric acid, oxalic acid, fumaric acid, maleic acid, succinic acid, glutaric acid, adipic acid, malic acid, lactic acid, citric acid, but also aromatic acids, such as, for example, benzoic acid and phthalic acid. The acids are added in amounts of 0.2 to 3 mol equivalents, preferably 1 to 2 mol equivalents, in each case based on the starting aminoisoindoline of the formula (VII) or (IX) used. However, large amounts of acid can also be used, preferably in those cases where the acid is simultaneously used as the solvent, for example acetic acid.

In a particularly preferred embodiment of the process for preparing compounds of the formula (II), the reaction is carried out in water or a water-containing medium. In addition to water, organic solvents can also be present, i.e. preferably those which are completely or partially miscible with water, such as, for example, alcohols, preferably those alcohols on which the radical $R_5$ is based, ketones, such as, for example, acetone, methyl ethyl ketone, cyclohexanone, ethers such as tetrahydrofuran and dioxane, dimethylformamide, N-methylpyrrolidone and the like. However, it is also possible to add to the aqueous reaction medium water-immiscible solvents, in order to improve, for example, crystallinity and to achieve specific crystal forms. The organic solvents can be present from the beginning or else can be added during the reaction. In this case too, it may be advantageous to add an organic acid, in order to accelerate the reaction and obtain improved crystallinity and a higher yield.

Carrying out the reaction in the presence of water or water-containing reaction media facilitates isolation of the dyestuffs and avoids workup of large amounts of organic solvents. In this process variant, the relative amounts of water used are preferably 20 to 100%, in particular 50 to 100% (relative to the amount of the reaction medium used).

If the reaction medium used is water or a predominantly aqueous medium, it is advantageous to add surface-active substances such as surfactants, dispersing agents, emulsifiers and wetting agents. Suitable substances are the known nonionic, anionic and cationic auxiliaries. Examples of such compounds are salts of alkylbenzenesulphonic acids, alkylphenolsulphonic acids, alkylnaphthalenesulphonic acids, condensation products of phenolsulphonic acids with formaldehyde and urea, lignosulphonates, addition products of ethylene oxide and propylene oxide with alkanols, alkanediols, phenols, carboxylic acids, amines, carboxamides and sulphuric monoesters thereof, it also being possible to use mixtures of these compounds. However, particular preference is given to lignosulphonate, such as, for example, kraft lignins, for example of the Reax® type from Westvaco or sulphite lignins, for example of the Ufoxane® type from Borregaard or mixtures thereof.

Depending on the type of materials used and the reaction medium, the condensation reactions can be carried out over a wide range of temperatures, but the preferred temperatures are between 40° C. and 120° C.

Very particular preference is also given to a process for preparing compounds of the formula (II) which is characterized in that the aminoisoindolenine compound of the formula (VII) or (IX) fused is prepared by condensation of amino-imino-isoindolenine of the formula (V)

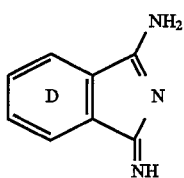

with the methine compounds of the formula (VI) or (VIII). This very particularly preferred process can be illustrated by the following reaction scheme:

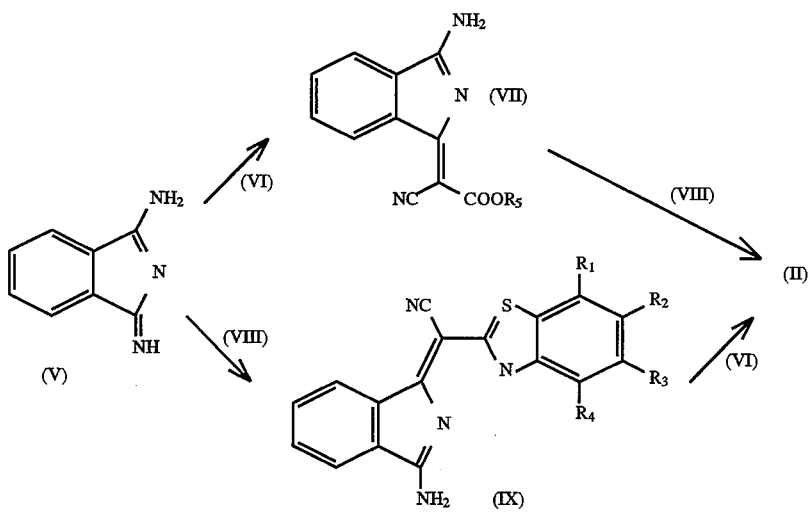

Accordingly, the above process for preparing dyestuffs of the formula (II) is preferably characterized in that the amino-isoindolenine of the formula (VII) used is obtained by reacting the amino-imino-isoindoline compound of the formula (V)

where D has the above meaning,
with a cyano acetic ester of the formula (VI)

NC—CH$_2$—COOR$_5$      (VI), where R$_5$ has the above meaning,
or the aminoisoindolenine of the formula (IX) used is obtained by reacting amino-imino-isoindoline of the formula (V) with a 2-cyanomethylbenzothiazole of the formula (VIII)

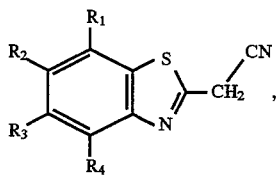

where R$_1$ to R$_4$ have the above meaning.

This process sequence according to the invention starting with the amino-imino-isoindoline compounds of the formula (V) to give the dyestuffs of the formula (II) can preferably also be carried out in water or a water-containing medium. In this procedure, it is in particular also possible to carry out a one-pot i.e. without isolation of the monocondensed amino-isoindolenine compound intermediates of the formula (VII) or (IX).

The process for preparing compounds of the formula (III) is characterized in that compounds of the formula (X)

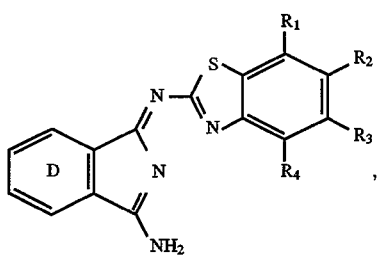

where D and R$_1$ to R$_4$ have the above meaning, are condensed with cyanoacetic esters of the formula (VI)

NC—CH$_2$—COOR$_5$      (VI), where R$_5$ has the above meaning.

The preferred reaction conditions of this preparation process are identical to those for the preparation of compounds of the formula (II). Surprisingly, in this case too, it was found that the condensation reaction under otherwise identical conditions can be carried out particularly advantageously in water or in mixtures of water with organic solvents.

Compounds of the formula (X) can be prepared in various ways. Thus, amino-imino-isoindolenines of the formula (V)

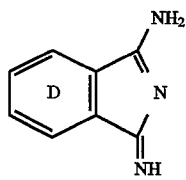

can be condensed with 2-amino-benzothiazoles of the formula (XI)

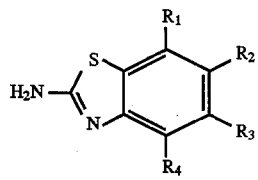

where $R_1$ to $R_4$ and D have the above meaning. Condensation of (V) and (XI) to give (X) can be effected by heating the components in an organic solvent, the solvent Used being, for example, amides such as formamide, dimethylformamide, dimethylacetamide and N-methylpyrrolidone and preferably alcohols, in particular lower alcohols such as methanol, ethanol, n-propanol and iso-propanol.

A further process for preparing compounds of the formula (X) has been found, which process is characterized in that 2-aminobenzothiazoles of the formula (XI)

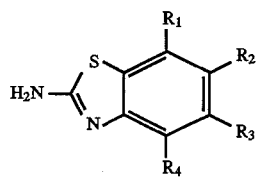

are reacted with phthalonitriles of the formula (XII)

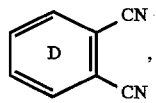

where $R_1$ to $R_4$ and D have the above meaning in the presence of a base.

This addition reaction can be carried out in an organic solvent, the solvents used being amides, such as, for example, formamide, dimethylformamide, dimethylacetamide and N-methylpyrrolidone, and preferably alcohols, and very particularly preferably lower alcohols, such as methanol, ethanol, n-propanol and iso-propanol. This reaction is preferably catalyzed by alcoholates such as sodium methoxide, sodium ethoxide, potassium tert.-butoxide. The amount of alcoholate can be varied within wide limits, but amounts between 0.5 and 1 mol equivalent, relative to the amount of (XII) used, are preferred.

Suitable reaction temperatures are between 0° and 100° C., preferably between 20 and 60° C. The advantage of this process for preparing compounds of the formula (X) is that no prior preparation of aminoiminoisoindolenine, which is usually prepared also from phthalonitrile, is necessary. This results in higher yields, in particular in higher space-time yields owing to the fact that the reaction proceeds very rapidly.

The process for preparing compounds of the formula (IV) is characterized in that aminoisoindolenines of the formula (IX)

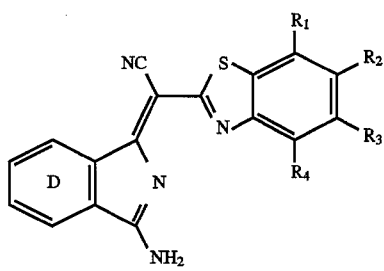

are reacted with amines of the formula $R_6$—$NH_2$ where D, $R_1$ to $R_4$ have the above meaning. In a preferred embodiment of this process, the preferred conditions such as described for preparing compounds of the formula (II) are chosen.

A preferred process for preparing compounds of the formula (IX) has already been described above.

A further process for preparing compounds of the formula (IV) is the reaction which is characterized in that compounds of the formula (XIII)

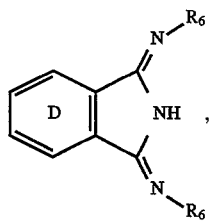

where $R_6$ and D have the above meaning, are reacted with compounds of the formula (VIII)

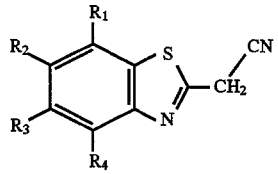

where $R_1$ to $R_4$ have the above meaning.

Preferred reaction conditions for these reactions are also the ones which have already been described for preparing compounds of the formula (II) and (IV).

The invention furthermore relates to the use of dyestuffs of the formula (I) for dyeing fully synthetic or semisynthetic high-molecular-weight materials where $R_6$ can additionally adopt the meaning of hydrogen and the compound excepted above is not excepted. This enlargement as compared with the dyestuffs applies to the following applications according to the invention. In order to avoid confusion, the enlarged scope of the general formula (I) is designated by (I+), that of (III) by (III+) and that of (IV) by (IV+), respectively. They are particularly suitable for dyeing or printing synthetic fibre materials, in particular those made of aromatic polyesters and/or cellulose acetates. The resulting dyeings possess a high colour strength and exhibit excellent light fastness, in particular high hot light fastness, and are therefore suitable in particular for dyeing and printing textile materials for the automotive industry and for dyeing so-called microfibres.

Dyestuffs of the formula (I+) are also highly suitable for thermal transfer printing on textile and non-textile substrates, for example by the D2T2 (dye diffusion thermal transfer process) for image recording. Furthermore, the dyestuffs can be used for the mass colouration of plastics, for example of polyethylenes, polypropylenes, polystyrene, polycarbonates, and of plastic blends such as, for example, ABS. Some of the dyestuffs, in particular those of the formulae (II) and (IV+) show fluorescence and are therefore also suitable as fluorescent dyestuffs.

Polyester textile materials can be dyed with the dyestuffs according to the invention by the spin dyeing method, but preferably from an aqueous suspension. To this end, the dyestuffs are processed in a generally known manner to give dyestuff preparations, for example by milling them in water in the presence of dispersing agents and/or fillers. The optionally vacuum-dried or spray-dried preparations can then be used, after addition of water, for dyeing, padding or printing in a short or long liquor.

Mixtures of at least two dyestuffs of the formulae (I+) to (IV+) are suitable in particular for dyeing polyester and can possibly improve the exhaustion and build-up properties of the dyestuff, their dispersibility and the levelling power.

A further advantage of the use of dyestuff mixtures compared with individual dyestuffs is the improved dyeing bath stability. If the dyeing bath stability is insufficient, the dyestuff(s) can precipitate from the dyeing bath under dyeing conditions, resulting in unlevel dyeings.

Of these, mixed crystals of at least two dyestuffs of the formulae (I+) to (IV+) such as can be formed, for example, in a joint synthesis are particularly preferred.

The dyestuff mixtures according to the invention can be prepared by various methods, for example by:

a) mixing the separately prepared and finished individual dyestuffs with one another, b) joint finishing of the separately prepared individual dyestuffs or c) joint synthesis of mixtures of dyestuffs from mixtures of different precursors where possible.

Mixing of the dyestuffs is advantageously carried out in suitable mills, for example ball or sand mills. However, individually finished dyestuffs can also be mixed by stirring them into dyeing liquors. To prepare or to improve the degree of dispersion of individual dyestuffs or mixtures, one or more dispersing agents are preferably added to the mixture to be milled or to the reaction mixture. It is of course also possible to influence the particle size of the dyestuff particles in a suitable manner and to adjust it to the desired value by means of a milling treatment, for example wet bead milling, either during synthesis or thereafter. Suitable dispersing agents for finishing the individual dyestuffs according to the invention and mixtures of at least two dyestuffs of the formula (I+) are in particular anionic and/or nonionic ones. Of these, anionic dispersing agents are preferred and a mixture of anionic and nonionic dispersing agents is particularly preferred.

Suitable anionic dispersing agents are in particular condensation products of aromatic sulphonic acids with formaldehyde, such as condensation products of formaldehyde and alkylnaphthalenesulphonic acids or of formaldehyde, naphthalenesulphonic acids and benzenesulphonic acids, condensation products of substituted or unsubstituted phenol with formaldehyde and sodium bisulphite. Furthermore, they include in particular lignosulphonates, for example those obtained by the sulphite or kraft process. They are preferably products which are partially hydrolyzed, oxidized, propoxylated, sulphonated, sulphomethylated or desulphonated and fractionated by known methods, for example by molecular weight or by degree of sulphonation. Mixtures of sulphite lignosulphonates and kraft lignosulphonates are particularly effective. Lignosulphonates having an average molecular weight of between 1,000 and 100,000, an active lignosulphonate content of at least 80% and, preferably, a low polyvalent cation content are particularly suitable. The degree of sulphonation may be varied over a wide range.

Examples of nonionic dispersing agents are reaction products of alkylene oxides with alkylatable compounds, such as, for example, fatty alcohols, fatty amines, fatty acids, phenols, alkylphenols, arylalkylphenols, carboxamides and resin acids. They are, for example, ethylene oxide adducts from the class of reaction products of ethylene oxide with a) saturated and/or unsaturated fatty alcohols having 6 to 20 C atoms or b) alkylphenols having 4 to 12 C atoms in the alkyl radical or c) saturated and/or unsaturated fatty amines having 14 to 20 C atoms or d) saturated and/or unsaturated fatty acids having 14 to 20 C atoms or e) hydrogenated and/or nonhydrogenated resin acids.

Suitable ethylene oxide adducts are in particular those obtained by reacting the alkylatable compounds mentioned in a) to e) with 5 to 30 mol of ethylene oxide.

The dyestuff preparations of the individual dyestuffs of the formula (I+) which are also according to the invention and mixtures thereof in general contain:

10–60% by weight of individual dyestuff/mixture

10–80% by weight of an anionic dispersing agent 0 to 15% by weight of a nonionic dispersing agent and, if desired, further additives, such as wetting agents, antifoams, dustproofing agents and further auxiliaries.

Examples of suitable wetting agents are $C_6$–$C_{10}$-alkyl phosphates or addition products of $C_6$–$C_{18}$-fatty alcohols with ethylene oxide and/or propylene oxide or mixtures of such alkoxylation products.

Examples of suitable antifoams are tributyl phosphate or tertiary acetyl glycol.

Examples of suitable dustproofing agents are those based on mineral oil.

Further auxiliaries are understood to mean, for example, fungicides, dryness inhibitors, and the like.

Preferred dyestuff preparations contain 10 to 50% by weight of individual dyestuff or dyestuff mixture 10 to 80% by weight of lignosulphonate, in particular kraft lignins and sulphite lignins 0 to 20% by weight of a condensation product of naphthalenesulphonic acid with formaldehyde, 0 to 10% by weight of a nonionic dispersing agent, in particular addition products of resin acids with ethylene oxide and/or propylene oxide, 0.1 to 1.5% by weight of wetting agent, 0.1 to 1% by weight of antifoam, 0.2 to 1.5% by weight of dustproofing agent, in each case relative to the entire preparation.

Of the dyestuff mixtures according to the invention, preference is given to those containing at least two dyestuffs of the formula (I+) in which the proportion of one dyestuff, relative to the mixture, is preferably 10–90% by weight and the proportion of the other dyestuff is preferably 90–10% by weight. Particularly preferred mixtures are those in which the proportion of one dyestuff, relative to the mixture, is 60–90% and the proportion of the other dyestuff is 10–40%.

Very particularly preferably, the dyestuff mixtures according to the invention are those containing at least two dyestuffs of the formulae (II) or (III) or at least one dyestuff of the formula (II) and at least one dyestuff of the formula (III). These are understood to mean in particular mixtures containing at least two dyestuffs of the formula (II) which differ from one another in one or more radicals $R_1$ to $R_5$, but preferably only by the radical $R_5$.

Equally preferred are dyestuff mixtures containing at least two dyestuffs of the formula (III) which differ from one another in one or more radicals $R_1$ to $R_5$, but preferably only by the radical $R_5$.

Particularly preferred mixtures contain at least two dyestuffs in which the radical $R_5$ represents $C_1$–$C_{20}$-alkyl in one dyestuff and a $C_1$–$C_{20}$-alkyl radical interrupted by oxygen atoms, in particular an alkoxyalkyl radical, in the second dyestuff. Examples of preferred alkyl radicals are ethyl, propyl, n-butyl, isobutyl, n-pentyl and n-hexyl. Examples of preferred alkoxyalkyl radicals are ethoxy-ethyl propyl-ethyl, iso-propoxyethyl and butoxyethyl.

Dyeing of the fibre material mentioned with the individual dyestuffs, dyestuff mixtures and the particular dyestuff preparations according to the invention is carried out in a manner known per se, preferably from an aqueous suspension, if appropriate in the presence of carriers in general at 80° to 110° C. by the exhaust method or at 110° to 140° C. in a dyeing autoclave by the HT method. This gives yellow to orange dyeings of very high colour strength and very good fastness properties. The individual dyestuff preparations or the preparations of the dyestuff mixtures according to the invention should be present in the dyeing liquors used in the above applications in very fine dispersion. Fine dispersion of the dyestuffs is carried out in a manner known per se by dispersing the individual dyestuffs or the dyestuff mixtures together with dispersing agents in a liquid medium, preferably in water, and subjecting the mixture to shearing forces, as a result of which the originally present dyestuff particles are comminuted mechanically to such an extent that an optimum specific surface area is obtained and sedimentation of the dyestuff is avoided if possible. In general, the particle sizes of the dyestuffs are between 0.1 and 5 μm, preferably between 0.5–0.1 μm. The dispersing agents used in the milling process can be the nonionic or anionic dispersing agents already mentioned in conjunction with the synthesis and preparation of the mixture.

For most areas of application, solid preparations (preparations of powders or granules) are preferred.

A preferred preparation process for solid dyestuff preparations consists in removing the liquid from the liquid dyestuff dispersions described above for example by vacuum drying, freeze drying, by drying on drum driers, but preferably by spray-drying.

To prepare the individual dyestuffs or dyestuff mixtures according to the invention in finely divided form, the procedure can be as follows: for example, 10 to 50 parts of an individual dyestuff or a dyestuff mixture according to the invention is milled together with 10 to 80 parts of lignosulphonate, 20 to 0 parts of the condensation product of naphthalenesulphonic acids with formaldehyde, 10 to 0 parts of nonionic dispersing agent, 0.1 to 1.5 parts of wetting agent, 0.1 to 1.0 part of antifoam, 0.2 to 1.5 parts of dustproofing agent in a pearl mill (parts=parts by weight).

The dyestuffs are also highly suitable for preparing mixtures with other disperse dyestuffs in order to produce, for example, brown, grey or green hues on the fibre since they do not impair the lightfastness of these dyestuffs.

A further preferred embodiment of the present invention relates to mixtures of one or more of the dyestuffs of the formulae (I+) to (IV+) with one or more dyestuffs such as are commonly used for dyeing polyester fibres or polyester textile materials for automotive cover fabrics. These dyestuffs for dyeing automotive cover fabrics can be in particular azo, disazo, anthraquinone, nitro, naphthalimide and terephthalimide dyestuffs. Particularly preferred dyestuffs for such mixtures are, for example, the Colour Index dyestuffs Yellow 23, 42, 51, 59, 65, 71, 86, 108, 122, 163, 182, 211, Orange 29, 30, 32, 41, 44, 45, 61, 73, Red 60, 82, 86, 91, 92, 127, 134, 138, 159, 167, 191, 202, 258, 279, 284, 302, 323, Blue 27, 54, 56, 60, 73, 77, 79, 79:1, 87, 266, 333, 361, Violet 27, 28, 57 and 95, the weight ratios of the dyestuff mixtures depending on the desired shade.

EXAMPLE 1

159.7 g (1.1 mol) of amino-imino-isoindolenine, 150.2 g (1.0 mol) of 2-aminobenzothiazole and 750 ml of ethanol are refluxed for 24 hours. After cooling to room temperature, the precipitated product is filtered off with suction and washed with ethanol and water. Drying at 70° C. gives 226.9 g (81.5% of theory) of a product of the formula:

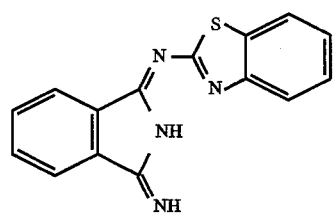

Analysis: $C_{15}H_{10}N_4S$ (molecular weight: 278.4)

|  | C | H | N | S |
| --- | --- | --- | --- | --- |
| % calculated | 64.7 | 3.6 | 20.1 | 11.5 |
| % found | 64.3 | 3.5 | 19.9 | 11.8 |

EXAMPLE 2

56.4 g (0.44 mol) of phthalonitrile, 60.1 g (0.4 mol) of 2-aminobenzothiazole and 300 ml of methanol are stirred, and 60 ml of a 30% strength solution of sodium methoxide in methanol are then added. The batch is stirred at 40° C. for 4 hours, during which a precipitate is already formed. Precipitation is completed by dropwise addition of 20.5 ml of glacial acetic acid. The product is filtered off with suction at room temperature and washed with methanol and water. Drying at 70° C. gives 102.1 g of a 90.8% pure product having the same structure as in Example 1. This corresponds to a yield of 90.8% of theory. The substance is sufficiently pure for further reactions.

EXAMPLE 3

Example 1 is repeated, replacing 2-aminobenzothiazole by an equivalent amount of 2-amino-6-methoxy-benzothiazole, to give a product of the formula:

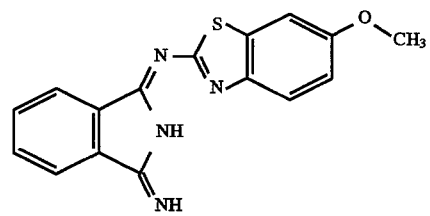

in a yield of 87.6% of theory.

EXAMPLE 4

Example 2 is repeated, replacing 2-aminobenzothiazole by an equivalent amount of 2-amino-6-methoxybenzothiazole, to give the same substance as in Example 3 in a yield of 91.6% of theory. The product is 97.6% pure.
Analysis: $C_{16}H_{12}N_4OS$ (molecular weight: 308.4)

|             | C    | H   | S    |
|-------------|------|-----|------|
| % calculated | 62.3 | 3.9 | 10.4 |
| % found      | 62.2 | 3.7 | 10.6 |

The substances of the formula X listed in Table 1 are obtained in comparable yield and purity by repeating the reactions of Examples 1 to 4 and using the corresponding substituted 2-amino-benzothiazoles.

TABLE 1

| Example No. | $R_1$ | $R_2$ | $R_3$ | $R_4$ |
|---|---|---|---|---|
| Ex. 5 | H | $OC_2H_5$ | H | H |
| Ex. 6 | H | $CH_3$ | H | H |
| Ex. 7 | $CH_3$ | | | $CH_3$ |
| Ex. 8 | H | H | $CH_3$ | H |
| Ex. 9 | Cl | $OCH_3$ | | $OCH_3$ |
| Ex. 10 | H | H | —CH=CH—CH=CH— | |

EXAMPLE 27.8 (0.1 mol) of a substance prepared according to Example 1 or an equivalent amount of a substance prepared according to Example 2, 400 ml of n-butanol, 17.3 ml (0.12 mol) of butyl cyanoacetate and 6 ml of glacial acetic acid are heated at 90° C. for 6 hours. After cooling to room temperature, the precipitated substance is filtered off with suction and washed with methanol and water. Drying gives 36.6 g (90.9% of theory) of a yellow dyestuff of the following formula, which dyes polyester fibres in greenish yellow shades having excellent lightfastness.

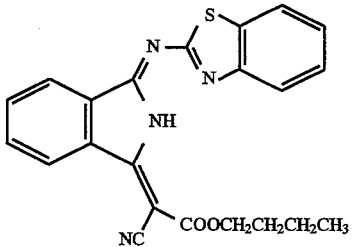

Analysis: $C_{22}H_{18}N_4O_2S$ (Molecular weight: 402.5)

|             | C    | H   | N    |
|-------------|------|-----|------|
| % calculated | 65.7 | 4.5 | 13.9 |
| % found      | 65.6 | 4.5 | 13.6 |

EXAMPLE 12

27.8 g (0.1 mol) of a substance prepared according to Example 1 or an equivalent amount of a substance prepared according to Example 2, 150 ml of water, 17.3 ml (0.12 mol) of butyl cyanoacetate and 6 ml of glacial acetic acid are heated at 95° C. for 4 hours. After cooling to room temperature, the precipitated substance is filtered off with suction and washed with methanol and water. Drying gives 39.4 g (97.9% of theory) of the same yellow dyestuff as in Example 11.

EXAMPLE 13

30.8 g (0.1 mol) of a substance prepared according to Example 3 or an equivalent amount of a substance prepared according to Example 4, 150 ml of water, 17.3 ml (0.12 mol) of amyl cyanoacetate, 20 ml of n-amyl alcohol and 6 ml of glacial acetic acid are heated at 95° C. for 4 hours. After cooling to room temperature, the precipitated substance is filtered off with suction and washed with methanol and water. Drying gives 44.1 g (98.7% of theory) of a yellow dyestuff of the following formula, which dyes polyester fibres in yellow-orange hues having excellent lightfastness.

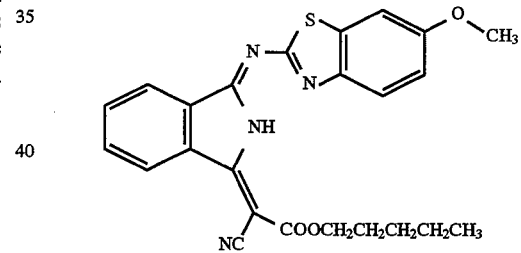

Dyestuffs of the formula III listed in Table 2 are obtained by repeating the procedures of Examples 11, 12 and 13, using the substances listed in Table 1 as starting materials, and condensing them with the corresponding esters of cyanoacetic acid.

TABLE 2

(Unless stated otherwise, $R_1$ to $R_4$ in the table represent hydrogen)

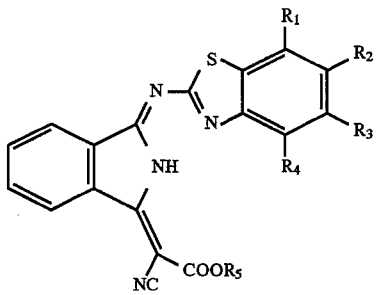

| Ex. No. | $R_1$ | $R_2$ | $R_3$ | $R_4$ | $R_5$ | Shade $\lambda_{max(DMF)}$ |
|---|---|---|---|---|---|---|
| Ex. 14 | | | | | n-Amyl | greenish yellow 413, 432 |
| Ex. 15 | | | | | n-Hexyl | greenish yellow |
| Ex. 16 | | | | | $-CH_2CH_2OCH_3$ | greenish yellow |
| Ex. 17 | | | | | $-CH_2CH_2OCH_2CH_3$ | greenish yellow |
| Ex. 18 | | $OCH_3$ | | | n-Butyl | yellowish orange |
| Ex. 19 | | $OCH_3$ | | | n-Hexyl | yellowish orange 440, 461 |
| Ex. 20 | | $OCH_3$ | | | $-CH_2CH_2OCH_3$ | yellowish orange |
| Ex. 21 | | $OCH_3$ | | | $-CH_2CH_2OCH_2CH_3$ | yellowish orange |
| Ex. 22 | | $OCH_3$ | | | $-CH_2CH_2OCH(CH_3)_2$ | yellowish orange |
| Ex. 23 | | $OCH_3$ | | | Benzyl | yellowish orange |
| Ex. 24 | | $OCH_3$ | | | Phenylethyl | yellowish orange |
| Ex. 25 | | $OC_2H_5$ | | | n-Butyl | yellowish orange |
| Ex. 26 | | $OC_2H_5$ | | | n-Amyl | yellowish orange |
| Ex. 27 | | $OC_2H_5$ | | | n-Hexyl | yellowish orange |
| Ex. 28 | | $CH_3$ | | | n-Butyl | greenish yellow |
| Ex. 29 | | $CH_3$ | | | n-Amyl | greenish yellow |
| Ex. 30 | | $CH_3$ | | | n-Hexyl | greenish yellow |
| Ex. 31 | $CH_3$ | | | $CH_3$ | n-Butyl | greenish yellow 416 |
| Ex. 32 | $CH_3$ | | | $CH_3$ | n-Amyl | greenish yellow 417 |
| Ex. 33 | $CH_3$ | | | $CH_3$ | n-Hexyl | greenish yellow |
| Ex. 34 | Cl | $OCH_3$ | | $OCH_3$ | $-CH_2CH_2O(CH_2)_3CH_3$ | yellowish orange 476 |
| Ex. 35 | Cl | $OCH_3$ | | $OCH_3$ | $-CH_2CH_2OCH(CH_3)_2$ | yellowish orange |
| Ex. 36 | Cl | $OCH_3$ | | $OCH_3$ | $-O(CH_2CH_2)_2-O(CH_2)_3CH_3$ | yellowish orange |
| Ex. 37 | | $-CH=CH-CH=CH-$ | | | n-Amyl | yellowish orange 475 |
| Ex. 38 | | $-CH=CH-CH=CH-$ | | | $-CH_2CH_2O(CH_2)_3CH_3$ | yellowish orange |

EXAMPLE 39

181.5 g (1.25 mol) of amino-imino-isoindolenine are dissolved in 2,500 ml of methanol, and 174.3 g of 2-cyanomethyl-benzothiazole is added. The batch is stirred at room temperature for 5 hours and at reflux for 2 hours. The precipitated product is then filtered off with suction at room temperature and washed with methanol to give 290.2 g (96% of theory) of a substance of the following formula:

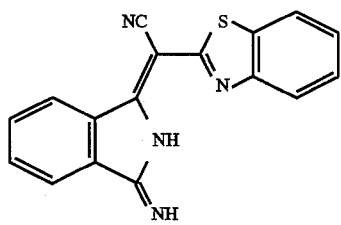

EXAMPLE 40

30.5 g (0.21 mol) of amino-imino-isoindolenine, 34.8 g (0.2 mol) of 2-cyanomethyl-benzothiazole, 200 ml of water and 1 g of Reax 910, which is a dispersing agent on the basis of sulpholignin, are stirred at room temperature for 3 hours, at 30° C. for 2 hours and at 40° C. for 1 hour. The solid is then filtered off with suction at 60° C. and washed with water to give 61.7 g of a product having the same structure as in Example 39.

EXAMPLE 41

28.2 g (0.22 mol) of phthalonitrile, 34.8 g (0.2 mol) of 2-cyanomethyl-benzothiazole and 200 ml of methanol are stirred, and 40 ml of a 30% strength sodium methoxide solution is added. The temperature rises to 40° C. over a period of 30 minutes with the formation of a dark precipitate. After 5 hours, the reaction mixture is acidified with 15 ml of glacial acetic acid, the solid is filtered off with suction and washed with methanol and water to give 55.3 g of a product having the same structure as in Example 39 and a purity of about 94%

EXAMPLE 42

The procedure for Example 41 is repeated, except that 22 ml of a 10N sodium hydroxide solution is used instead of sodium methoxide, to give 55.9 g of a product having the same structure as in Example 39 and a purity of about 93.6%.

The substances of the formula IX listed in Table 3 are obtained in comparable yield and purity by repeating the reactions of Examples 39 to 42 but using the corresponding substituted 2-cyanomethyl-benzothiazoles.

TABLE 3

| Example No. | $R_1$ | $R_2$ | $R_3$ | $R_4$ | $\lambda_{max}$ (DMF) |
|---|---|---|---|---|---|
| Ex. 43 | | $OCH_3$ | | | 447 nm |
| Ex. 44 | | $OC_2H_5$ | | | 447 nm |
| Ex. 45 | | $CH_3$ | | | |
| Ex. 46 | | | $CH_3$ | | 438 nm |
| Ex. 47 | $OCH_3$ | | | | |
| Ex. 48 | | | | $OCH_3$ | |

EXAMPLE 49

60.5 g (0.2 mol) of a substance prepared according to Example 39 or an equivalent amount of a substance prepared according to Examples 40 to 42, 4.8 g of Reax 910, 200 ml of water and 12 ml of glacial acetic acid are stirred. To this mixture are added 42.6 g (0.23 mol) of 2-butoxy-ethyl cyanoacetate and 30 ml of 2-butoxyethanol, and the batch is heated at 80° C. for 3 hours and at 95° C. for 2 hours. The product is then filtered off with suction and washed with water to give 89.8 g of a substance of the following formula which is 88% pure by HPLC and has a $\lambda_{max}$ (DMF+5% of glacial acetic acid) of 458 nm. The dyestuff dyes polyester materials in yellow, fluorescent shades having very high lightfastness.

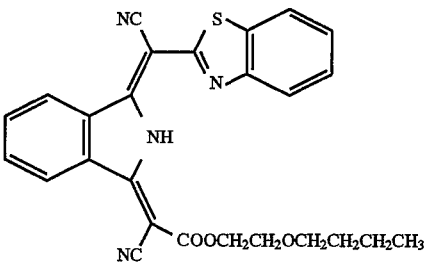

EXAMPLE 50

42.6 g (0.23 mol) of 2-butoxy-ethyl cyanoacetate, 60.5 g (0.2 mol) of a substance prepared according to Example 39 or an equivalent amount of a substance according to Examples 40 to 42, 12 ml of glacial acetic acid and 500 ml of 2-butoxy-ethanol are heated at 80° C. for 3 hours. This gives 84.8 g of a substance having the same structure as in Example 49.

EXAMPLE 51

30.5 g (0.21 mol) of amino-imino-isoindolenine, 34.8 g (0.2 mol) of 2-cyanomethyl-benzothiazole, 2 g of Reax 910 and 200 ml of water are stirred at 30° C. for 3 hours and at 40° C. for 1 hour. 2 g of Reax 910, 24 ml of glacial acetic acid, 44.4 g (0.24 mol) of 2-butoxy-ethyl cyanoacetate and 30 ml of 2-butoxy-ethanol are then added, and the mixture is heated at 80° C. for 2 hours and at 90° C. for 2 hours. The product is then filtered off with suction and washed with water to give 94.8 g of a substance having the same structure as in Example 50 and an HPLC purity of 71%.

The dyestuffs of the formula II listed in Table 4 are obtained by repeating the procedures of Examples 49 and 50, using the substances listed in Table 3 as the starting materials, and condensing them with the corresponding esters of cyanoacetic acid.

TABLE 4

| | (Unless stated otherwise, $R_1$ to $R_4$ in the table represents hydrogen) | | | | | |
|---|---|---|---|---|---|---|
| Ex. No. | $R_1$ | $R_2$ | $R_3$ | $R_4$ | $R_5$ | Shade $\lambda_{max}$ |
| Ex. 52 | | | | | n-Butyl | |
| Ex. 53 | | | | | n-Amyl | |
| Ex. 54 | | | | | n-Hexyl | |
| Ex. 55 | | | | | —$CH_2CH_2OCH(CH_3)_2$ | |
| Ex. 56 | | $OCH_3$ | | | n-Hexyl | reddish orange |
| Ex. 57 | | $OCH_3$ | | | —$CH_2CH_2O(CH_2)_3CH_3$ | reddish orange 467,499 nm |
| Ex. 58 | | $CH_3$ | | | —$CH_2CH_2O(CH_2)_3CH_3$ | yellow 467,499 nm |
| Ex. 59 | | | $CH_3$ | | —$CH_2CH_2O(CH_2)_3CH_3$ | yellow 462 nm |
| Ex. 60 | | $OC_2H_5$ | | | n-Amyl | reddish orange |
| Ex. 61 | | $OC_2H_5$ | | | n-Hexyl | reddish orange 478 nm |
| Ex. 62 | | $OC_2H_5$ | | | —$CH_2CH_2O(CH_2)_3CH_3$ | reddish orange |

EXAMPLE 63

34.6 g of the substance from Example 44, 11 ml of n-butylamine, 6 ml of glacial acetic acid and 250 ml of n-butanol are heated at 80° C. for 2 hours and at reflux for 3 hours. The product is filtered off with suction at room temperature and recrystallized from DMF/water to give 28 g of a product of the following formula which dyes polyester fibres in greenish yellow shades. In DMF, the product has an absorption maximum at 448 nm.

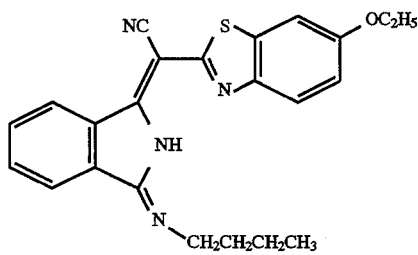

The compounds of the general formula (IV) listed in Table 5 can be prepared by repeating the procedure of Example 63.

TABLE 5

(Unless stated otherwise,
$R_1$ to $R_4$ in the table represents hydrogen)

| Ex. No. | $R_1$ | $R_2$ | $R_3$ | $R_4$ | $R_5$ | Shade $\lambda_{max}$ (DMF) |
|---|---|---|---|---|---|---|
| 64 | | $CH_3$ | | | n-Hexyl | greenish yellow 443 nm |
| 65 | | | $CH_3$ | | n-Butyl | greenish yellow 438 nm |
| 66 | | $OCH_3$ | | | n-Hexyl | greenish yellow 450 nm |
| 67 | | $OC_2H_5$ | | | n-Butyl | greenish yellow 448 nm |
| 68 | | $OC_2H_5$ | | | n-Hexyl | greenish yellow 451 nm |
| 69 | | $OC_2H_5$ | | | —$CH_2CH_2OCH_3$ | greenish yellow |

EXAMPLE 70

70a) 159.7 g (1.1 mol) of amino-imino-isoindolenine, 150.2 g (1.0 mol) of 2-aminobenzothiazole and 750 ml of ethanol are refluxed for 24 hours. After cooling to room temperature, the precipitated product is filtered off with suction and washed with ethanol and water. Drying at 70° C. gives 226.9 g (81.5% of theory) of a product of the formula:

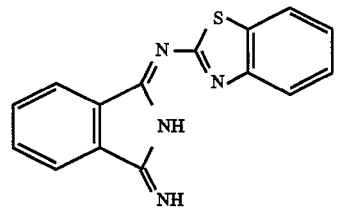

Analysis: $C_{15}H_{10}N_4S$ (Molecular weight: 278.4)

| | C | H | N | S |
|---|---|---|---|---|
| % calculated | 64.7 | 3.6 | 20.1 | 11.5 |
| % found | 64.3 | 3.5 | 19.9 | 11.8 |

70b) 27.8 g (0.1 mol) of a substance prepared according to Example 70a, 400 ml of n-butanol, 17.3 ml (0.12 mol) of butyl cyanoacetate and 6 ml of glacial acetic acid are heated at 90° C. for 6 hours. After cooling to room temperature, the precipitated substance is filtered off with suction and washed with methanol and water. Drying gives 36.6 g (90.9% of theory) of a yellow dyestuff of the formula

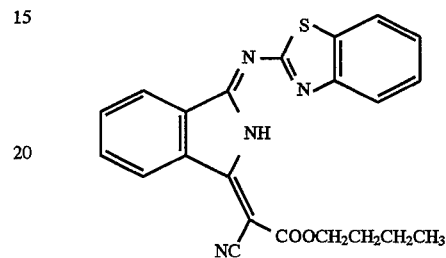

70c) The procedure of Example 70b is repeated, except that the butyl cyanoacetate is replaced by an equivalent amount of 2-butoxy-ethyl cyanoacetate and n-butanol is replaced by the same volume of 2-butoxy-ethanol, to give the dyestuff of the formula

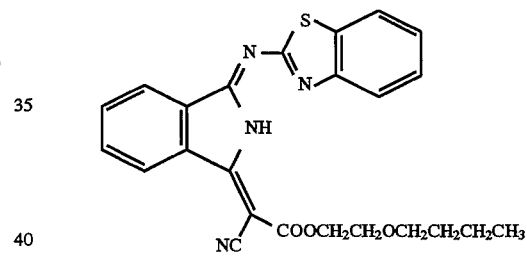

in comparable yield.

70d) 27.8 g (0.1 mol) of a substance prepared according to Example 70a, 150 ml of water, 18.3 g (0.12 mol) of a mixture of 75% of butyl cyanoacetate and 25% of 2-butoxy-ethyl cyanoacetate and 6 ml of glacial acetic acid are heated at 95° C. for 4 hours. After cooling to room temperature, the precipitated substance is filtered off with suction and washed with methanol and water. Drying gives 39.4 g of a mixture of the two dyestuffs of Examples 70b and 70c.

Finishes 70e) 63 g of sodium lignosulphonate and 3 g of a nonionic dispersing agent (addition product of abietic acid and 50 mol equivalents of ethylene oxide) are added to 30 g of the dyestuff obtained in Example 70b (in the form of the water-moist presscake) in 200 ml of water, and the resulting mixture is brought to a pH of 7 by addition of 25% sulphuric acid. This is followed by 1 hour of milling at room temperature in a pearl mill until fine dispersion (90% ≦ 1 μm) is achieved, screening and drying in a spray-drier.

70f) The procedure of Example 70e is repeated, except that the dyestuff 70b is replaced by the dyestuff 70c.

70g) The procedure of Example 70e is repeated, except that 8.0 g of the 30 g of dyestuff 70 b is replaced with the dyestuff from Example 70c, to give a mixed finish.

70h) 63 g of sodium lignosulphonate and 1.5 to 6 g of the nonionic dispersing agent from Example 70e are added to 25.5 to 21.0 g of the dyestuff from Example 70b and 4.5 to 9.0 g of the dyestuff from Example 70c in 200 ml of water. This is followed by 1 hour of milling in a pearl mill until fine dispersion (90%≦1 μm) is achieved, during which the temperature was raised to 80° to 90° C. for about 15 minutes. The respective dyestuff mixtures were screened and spray-dried.

70i) The two dyestuffs from Examples 70b and 70c are replaced by 30 g of the mixed dyestuff from Example 70d. Apart from that, the finishing process is carried out as in Example 70e.

Use Example 1

2 g of the powder obtained according to Example 70e is dispersed in 1,000 g of water. 0.5 to 2 g/l of a commercially available dispersing agent based on a condensation product of the sodium salt of naphthalenesulphonic acid with formaldehyde, 0.5 to 2 g/l of monosodium phosphate and 2 g of a commercially available levelling agent are added to the dispersion, and the resulting mixture is brought to a pH of 4.5 to 5.5 with acetic acid. The dyeing liquor thus obtained is entered with 100 g of a textured polyester fabric based on polyethylene glycol terephthalate, and the material is dyed at 130° C. for 60 minutes.

The dyestuff preparations obtained according to Examples 70f to 70i were also used for dyeing following the same method. In particular during the heating phase between 90° and 100° C., the dyestuff mixtures showed significantly improved dyeing bath stability compared with the individual dyestuffs.

EXAMPLE 71

71a) 181.5 g (1.25 mol) of amino-imino-isoindolenine is dissolved in 2,500 ml of methanol, and 174.3 g of 2-cyanomethyl-benzothiazole is added. The batch is stirred at room temperature for 5 hours and at reflux for 2 hours. The precipitated product is then filtered off with suction at room temperature and washed with methanol to give 290.2 g (96% of theory) of a substance of the following formula

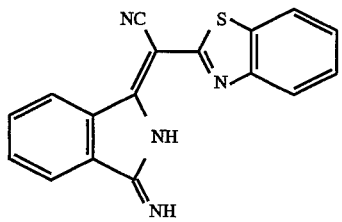

71b) 60.5 g (0.2 mol) of a substance prepared according to Example 71a), 4.8 g of Reax® 910, 200 ml of water and 12 ml of glacial acetic acid are stirred. To this mixture are added 42.6 g (0.23 mol) of 2-butoxy-ethyl cyanoacetate and 30 ml of 2-butoxy-ethanol, and the batch is heated at 80° C. for 3 hours and at 95° C. for 2 hours. The product is then filtered off with suction and washed with water to give 89.8 g of a substance of the following formula having an HPLC purity of 88% and a $\lambda_{max}$ (DMF+5% of glacial acetic acid) of 458 nm. The dyestuff dyes polyester materials in yellow fluorescent shades having very high lightfastness.

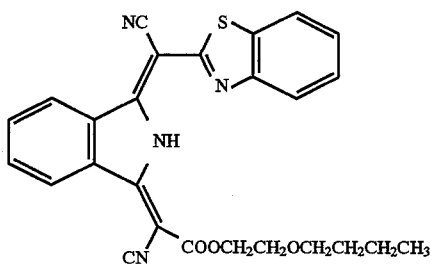

71c) The procedure of Example 71b is repeated, except that the 2-butoxy-ethyl cyanoacetate is replaced by an equivalent amount of the amyl ester, to give the dyestuff of the formula

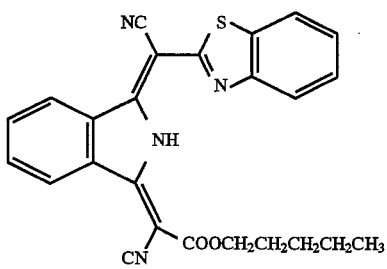

in a comparable yield.

71d) The procedure of Example 71b is repeated, except that the 2-butoxy-ethyl cyanoacetate is replaced by an equivalent mixture of 75% of the 2-butoxy-ethyl cyanoacetate and 25% of the amyl ester, to give directly a mixture of the two dyestuffs from Examples 71b and 71d in comparable yields.

Use Example 2

The procedure of Use Example 1 is repeated, except that the dyestuffs are replaced by the corresponding dyestuffs from Examples 70 and 71, to give likewise strong brilliant yellow dyeings having excellent colouristic properties, the thermostability of the dyestuff dispersions in the dyeing bath also being significantly improved compared with the corresponding dispersions of the individual dyestuffs.

We claim:

1. Dyestuffs of the formula (I)

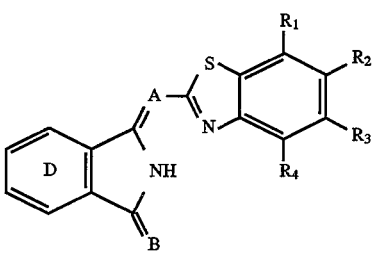

in which

A represents a cyanomethylene radical,

B represents a radical of the formula $C(CN)COOR_5$ or $N-R_6$, $R_1$ to $R_4$, independently of one another, denote hydrogen, halogen, substituted or unsubstituted $C_1-C_8$-alkyl or $C_5-C_8$-cycloalkyl, uninterrupted or oxygen-interrupted $C_1-C_{10}$-alkoxy, substituted or unsubtituted $C_6-C_{10}$-aryloxy, $CF_3$, or substituted or unsubstituted dialkylamine, or any two adjacent $R_1$ to $R_1$ radicals together with the aromatic ring C atoms form a fused benzene or naphthalene ring which is further unsubsituted or substituted, $R_5$ represents a substituted or unsubstituted, uninterrupted of oxygen-interrupted, saturated or unsaturated $C_1$–$C_{20}$-alkyl radical, $C_6$–$C_{10}$-aryl-$C_1$–$C_{10}$-alkyl or hetarylalkyl $R_6$ represents substituted or unsubstituted, uninterrupted or oxygen-interrupted $C_1$–$C_{20}$-alkyl, cycloalkyl, cycloalkyl-alkyl, or aralkyl, and ring D is unsubstituted or carries at least one substituent which, if desired, together with a further substituent in the o position and the ring C atoms forms a fused benzene or naphthalene ring, or A represents N, $R_5$ represents a substituted or unsubstituted, uninterrupted or oxygen-interrupted, sautrated or unsaturated $C_4$–$C_{20}$ alkyl radical, $C_6$–$C_{10}$-aryl-$C_1$–$C_{10}$-alkyl or hetarylalkyl and B, $R_1$ to $R_4$, $R_6$ and D have the above mentioned meanings.

2. Dyestuffs of the formula (1) according to claim 1, in which

A represents a cyanomethylene radical, $R_1$ and $R_2$, independently of one another, denote hydrogen, Cl, Br, methyl, ethyl, n-propyl, isopropyl, n-butyl, iso-butyl, tert-butyl, cyclohexyl, $C_1$–$C_{10}$-alkoxy which may be interrupted by 1 to 2 oxygens, substituted or unsubstituted phenoxy, $CF_3$ or a di($C_1$–$C_4$)-alkylamino group, $R_3$ and $R_4$ have the meaning of $R_1$ and $R_2$ or together with the ring C atoms form a fused benzene ring, $R_5$ denotes $C_1$–$C_{12}$-alkyl, $C_6$–$C_{10}$-aryl-$C_1$–$C_{10}$-alkyl or hetarylalkyl which is unsubstituted or substituted by Cl, CN or substituted or unsubstituted phenoxy and may be interrupted by 1 to 2 oxygen atoms, $R_6$ denotes saturated or unsaturated $C_1$–$C_{12}$-alkyl which is unsubstituted or substituted by substituted or unsubstituted phenoxy and may be interrupted by 1 to 2 oxygens, and ring D is unsubstituted or substituted by CN, halogen atoms, in particular 1 to 4 Cl atoms, 1 to 2 $C_1$–$C_{10}$-alkyl radicals and/or 1 to 2 $C_1$–$C_{10}$-alkoxy radicals, or a phenyl radical, each of which is uninterrupted or interrupted by 1 to 2 oxygen atoms, or A represents N, $R_5$ denotes $C_4$–$C_{12}$-alkyl, $C_6$–$C_{10}$-aryl-$C_1$–$C_{10}$-alkyl or hetarylalkyl which is unsubsituted or substituted by Cl, CN or substituted or unsubstituted phenoxy and may be interrupted by 1 to 2 oxygen atoms, and B, $R_1$ to $R_4$, $R_6$ and D have the above mentioned meanings.

3. Dyestuffs according to claim 1 the formula (II)

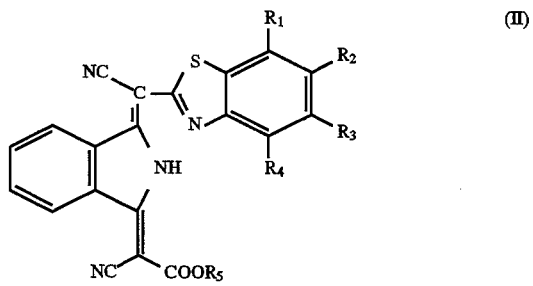

in which $R_1$ to $R_5$ have the meanings according to claim 1.

4. Dyestuffs according to claim 1 of the formula (III)

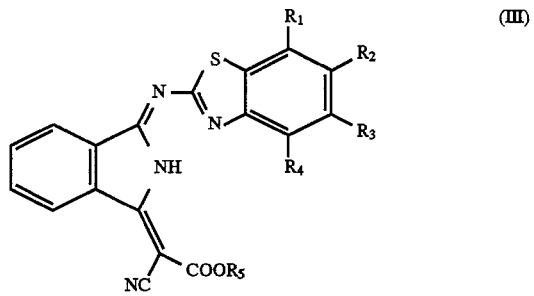

in which $R_1$ to $R_5$ have the meanings according to claim 1.

5. Dyestuffs according to claim 1 of the formula (IV)

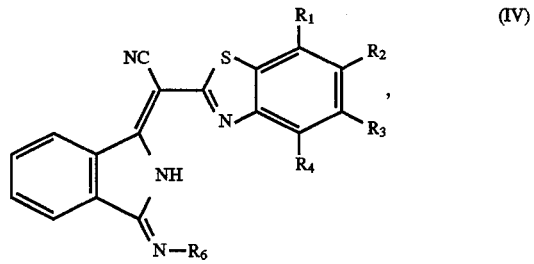

in which $R_1$ to $R_4$ and $R_6$ have the meanings given in claim 1.

* * * * *

UNITED STATES PATENT AND TRADEMARK OFFICE
CERTIFICATE OF CORRECTION

PATENT NO. : 5,646,290
DATED : July 8, 1997
INVENTOR(S) : Lorenz, et al.

It is certified that error appears in the above-indentified patent and that said Letters Patent is hereby corrected as shown below:

Col. 25, line 1  Delete " $R_1$ to $R_1$ " and substitute -- $R_1$ to $R_4$ --

Signed and Sealed this

Twenty-eighth Day of April, 1998

Attest:

BRUCE LEHMAN

*Attesting Officer*    *Commissioner of Patents and Trademarks*